(12) United States Patent
Okiyama

(10) Patent No.: US 11,523,741 B2
(45) Date of Patent: Dec. 13, 2022

(54) INTRAORAL IMAGING APPARATUS, MEDICAL APPARATUS, AND PROGRAM

(71) Applicant: AILLIS INC., Tokyo (JP)

(72) Inventor: Sho Okiyama, Tokyo (JP)

(73) Assignee: AILLIS INC.

( * ) Notice: Subject to any disclaimer, the term of this patent is extended or adjusted under 35 U.S.C. 154(b) by 250 days.

(21) Appl. No.: 16/958,085

(22) PCT Filed: Dec. 18, 2018

(86) PCT No.: PCT/JP2018/046559
§ 371 (c)(1),
(2) Date: Jun. 25, 2020

(87) PCT Pub. No.: WO2019/131327
PCT Pub. Date: Jul. 4, 2019

(65) Prior Publication Data
US 2021/0059534 A1    Mar. 4, 2021

(30) Foreign Application Priority Data
Dec. 28, 2017   (JP) .............................. JP2017-254164

(51) Int. Cl.
*A61B 5/00* (2006.01)
(52) U.S. Cl.
CPC .......... *A61B 5/0088* (2013.01); *A61B 5/0062* (2013.01); *A61B 5/742* (2013.01)
(58) Field of Classification Search
CPC ..... A61B 5/0062; A61B 5/0088; A61B 5/742; A61B 1/32; A61B 1/00059;
(Continued)

(56) References Cited

U.S. PATENT DOCUMENTS

| 7,303,528 B2 | 12/2007 | Couvillon, Jr. |
| 2016/0287063 A1 | 10/2016 | Ramanujam et al. |

(Continued)

FOREIGN PATENT DOCUMENTS

| CA | 2791624 | * 9/2011 |
| JP | 2015-213733 A | 12/2015 |

(Continued)

OTHER PUBLICATIONS

Yamada, Masayoshi et al.: "Development of real-time endoscopic image automatic analysis system for finding colorectal cancer and pre-cancerous lesions using an artificial intelligence system based on quantification of shape information"; Sep. 15, 2017; Nippon Shokakibyo Gakkai Zasshi; vol. 114; p. A498; ISSN 0446-6586; special extra edition (conference) (2pages).

(Continued)

*Primary Examiner* — Robert Chevalier
(74) *Attorney, Agent, or Firm* — Harness, Dickey & Pierce, P.L.C.

(57) ABSTRACT

An intraoral imaging apparatus, a medical apparatus, and a program capable of providing auxiliary data for determination regarding diseases having differences in intraoral findings are provided. The intraoral imaging apparatus includes: an imaging device that acquires an intraoral image; a light source that emits light to a subject of the imaging device; a storage apparatus that stores an algorithm for performing determination of a specific disease; and an arithmetic apparatus, in which the arithmetic apparatus executes: a determination process of determining a possibility of the predetermined disease based on the image and the algorithm; and an output process of outputting a result of the determination process.

12 Claims, 16 Drawing Sheets

(58) Field of Classification Search
CPC . A61B 1/00135; A61B 1/24; A61B 1/000096; A61B 1/00154; A61B 1/0638; A61B 1/267; G06T 7/0012; G06T 2207/10068; G06T 2207/20081; G06T 2207/30168; G06T 2207/30092; G06T 2207/24
USPC ......... 600/300, 301, 309; 386/210, 223, 224
See application file for complete search history.

(56) References Cited

U.S. PATENT DOCUMENTS

2017/0007126 A1 1/2017 Shahar
2017/0172418 A1 6/2017 Munro et al.

FOREIGN PATENT DOCUMENTS

| KR | 200171384 Y1 | 3/2000 |
| KR | 200395743 Y1 | 9/2005 |
| WO | 2016-185463 A1 | 11/2016 |
| WO | 2019-092723 A1 | 5/2019 |

OTHER PUBLICATIONS

Miyamoto, Akihiko and Shigeyuki Watanabe: "Posterior Pharyngeal Wall Follicles as a Diagnostic Marker of Influenza During Physical Examination: Considering Their Meaning and Value"; J. Nihon Univ. Med. Assoc; Jan. 9, 2013; vol. 72(1); pp. 11-18.

* cited by examiner

INTRAORAL IMAGING APPARATUS, MEDICAL APPARATUS, AND PROGRAM

CROSS REFERENCE TO RELATED APPLICATIONS

This application is a U.S. National Phase Application of International Application No. PCT/JP2018/046559, filed on Dec. 18, 2018, which claims priority to Japanese Application No. 2017-254164, filed on Dec. 28, 2017. The entire disclosures of the above applications are incorporated herein by reference.

BACKGROUND

Technical Field

The present invention relates to an intraoral imaging apparatus configured to perform intraoral imaging, a medical apparatus including the intraoral imaging apparatus and an intraoral imaging aid, and a program used for determination of a predetermined disease based on a captured intraoral image.

RELATED ART

Miyamoto/Watanabe, "Posterior Pharyngeal Wall Follicles as a Diagnostic Marker of Influenza During Physical Examination: Considering Their Meaning and Value", Journal of Nihon University Medical Association 72(1): 11-18 (2013) reports that lymph follicles appearing at the deepest part of the pharynx have a pattern peculiar to influenza. Lymph follicles having such a pattern will be referred to as influenza follicles. Influenza follicles are a characteristic sign of influenza and are considered to appear about two hours after the onset.

Accurate discrimination of influenza follicles is expected to lead to a dramatic improvement in diagnostic accuracy. However, appropriate diagnostic decision of influenza follicles requires intensive training through a large number of cases and is never easy for general physicians. Unfortunately, the findings of the above studies have only been utilized among a limited number of physicians to good effect.

Here, there are many diseases, other than influenza, having differences in pharyngeal findings. The points made in the above can also apply to diagnosis of such diseases.

Furthermore, diagnostic imaging is also useful for the diseases having differences in intraoral findings.

Therefore, the present invention aims to provide an intraoral imaging apparatus, a medical apparatus, and a program capable of providing auxiliary data for determination regarding the diseases having differences in intraoral findings.

SUMMARY

In order to solve the above-described problems, the present invention provides an intraoral imaging apparatus which is an imaging apparatus including: an imaging device that acquires an intraoral image; a light source that emits light to a subject of the imaging device; a storage apparatus that stores an algorithm for performing determination of a specific disease; and an arithmetic apparatus, in which the arithmetic apparatus executes: a determination process of determining a possibility of the predetermined disease based on the image and the algorithm; and an output process of outputting a result of the determination process.

Here, "intraoral" shall include the oral cavity and pharynx of all animals including humans. In addition, "pharynx" shall also include the "Waldeyer's Ring" including lymph follicles on the posterior pharyngeal wall. Accordingly, the "patient" in the present invention includes not only humans but animals in general.

Furthermore, the light source include a wide variety of devices capable of imaging, and accordingly the light source may emit either visible light or invisible light such as near-infrared rays or infrared rays.

In the intraoral imaging apparatus according to the present invention configured as above, the imaging device may acquire a moving image as the image, and the arithmetic apparatus may further execute an extraction process of extracting at least one still image that satisfies a predetermined condition from among a plurality of still images included in the moving image and may execute the determination process based on a result of the extraction process. Here, acquisition of a moving image means capturing an image using an imaging device, and this may include or need not include recording of a captured image to a recording medium. In addition, the predetermined condition may be a condition regarding data content of the image or a condition regarding a timing of image extraction.

Furthermore, the intraoral imaging apparatus according to the present invention configured as above may further include an input apparatus that receives input of patient information, and the arithmetic apparatus may execute the determination process further based on the patient information.

Furthermore, the intraoral imaging apparatus according to the present invention configured as above may further include a display apparatus that displays at least one of the image acquired by the imaging device or the result of the extraction process.

Furthermore, in the intraoral imaging apparatus according to the present invention configured as above, the imaging device may acquire the intraoral image at a position inside an intraoral imaging aid having a tubular shape to be attached to the inside of the mouth, the storage apparatus may store identification information of an intraoral imaging aid that has already been used, and the arithmetic apparatus may further execute an acquisition process of acquiring identification information of an intraoral imaging aid to be used for new determination, a search process of searching the presence or absence of a record of the storage apparatus that matches the identification information of an intraoral imaging aid to be used for new determination, and a restriction process of restricting the new determination depending on a result of the search process.

The present invention also provides a medical apparatus that includes the above-described intraoral imaging apparatus and an intraoral imaging aid having a tubular shape and configured to be detachably attached to the inside of the mouth, in which the intraoral imaging aid includes: a first end having an opening; and a second end located on an opposite side of the first end and having a window that provides a visual field from the inside to the outside of the intraoral imaging aid.

The present invention also provides a program causing a computer, the computer equipped with a storage apparatus storing an algorithm for performing determination of a specific disease and an arithmetic apparatus, to execute a determination process of determining a possibility of the predetermined disease based on an intraoral image acquired by the imaging device and based on the algorithm and an output process of outputting a result of the determination process.

Advantageous Effects of Invention

According to the present invention, it is possible to provide auxiliary data for determination regarding the diseases having differences in intraoral findings.

DETAILED DESCRIPTION

Figure 1:
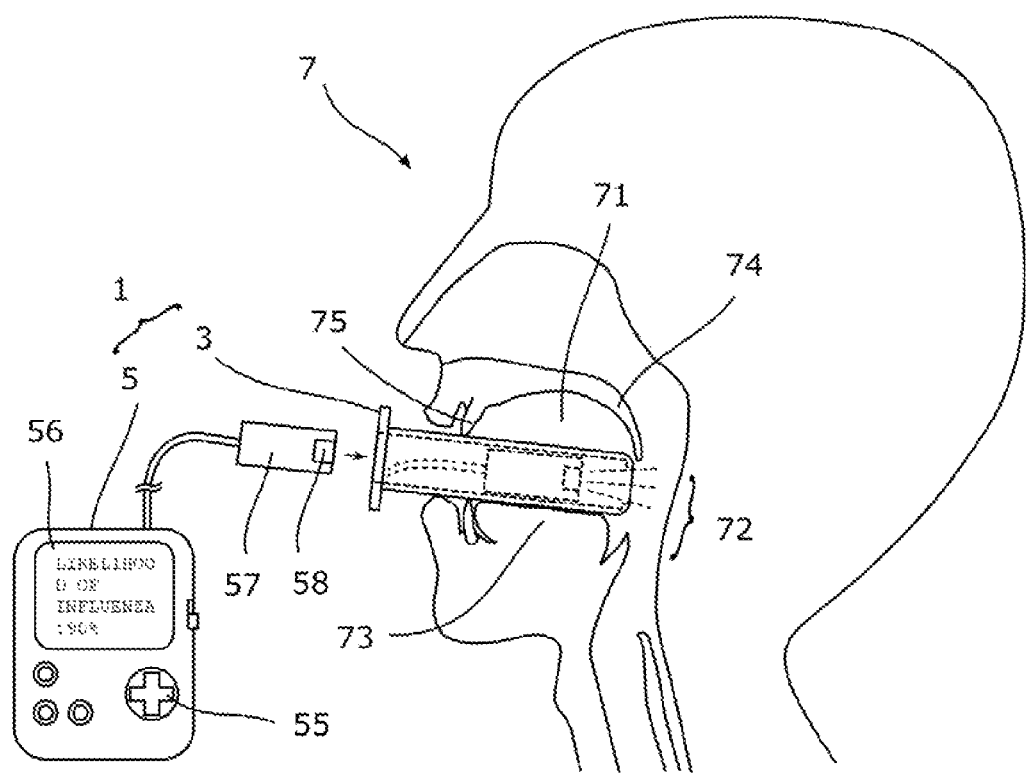
FIG. 1 is a schematic view of a medical apparatus 1 including an intraoral imaging apparatus 5 and an intraoral imaging aid 3 according to a representative embodiment of the present invention.

Hereinafter, a medical apparatus including an intraoral imaging apparatus and an intraoral imaging aid according to a representative embodiment of the present invention will be described in detail with reference to the drawings. However, the present invention is not limited to such embodiments and drawings. Furthermore, since the drawings are provided for conceptual representation of the present invention, and thus use dimensions, ratios, or numbers that are exaggerated or simplified as necessary to facilitate understanding.

Furthermore, while the following disclosure assumes the use of the medical apparatus for determination of influenza, the present invention is not limited to this. For example, there are many diseases such as streptococcal infections, adenovirus infections, EB virus infections, *mycoplasma* infections, or the like, having differences in pharyngeal findings. Moreover, important findings might appear in the oral cavity in these diseases as well. Furthermore, findings might appear in the oral cavity due to a disease other than these diseases. The medical apparatus may be used for determination of any disease that presents findings in the pharynx and oral cavity in this manner. Moreover, the intraoral imaging aid may be used in combination with other devices such as a smartphone and a tablet terminal.

1. Overview of Medical Apparatus

An outline of a medical apparatus 1 of the present embodiment will be described with reference to FIG. 1. As illustrated in the figure, the medical apparatus 1 includes an intraoral imaging apparatus 5 and an intraoral imaging aid 3. The intraoral imaging apparatus 5 is preferably used in combination with the intraoral imaging aid 3, though it may be used alone or in combination with other aids.

The intraoral imaging apparatus 5 includes an imaging device 57 that acquires an image of a subject, and the apparatus 5 has preinstalled dedicated software. A user (for example, a physician) instructs a determination subject 7 (for example, a patient) suspected of being infected with influenza to hold the intraoral imaging aid 3 in the mouth to ensure a visual field for imaging. Thereafter, the user inserts the imaging device 57 into the intraoral imaging aid 3 and images a pharynx 72 of the subject 7. The user can also capture an image of the oral cavity 71 of the subject 7 by adjusting the insertion depth and the insertion angle of the intraoral imaging aid 3. Alternatively, the user may insert the intraoral imaging aid 3 having the imaging device 57 housed therein into the mouth of the determination subject 7, or may instruct the determination subject 7 to insert the intraoral imaging aid 3 into the mouth.

The captured image is processed by a determination algorithm generated in advance. Although such process is supposed to be performed by the intraoral imaging apparatus 5, it may be performed by another computer. For example, when the determination is related to the possibility of influenza, the determination algorithm detects a pharyngeal symptom (pattern) unique to influenza such as influenza follicles and displays the likelihood of influenza. This makes it possible for even an inexperienced physician or a clinical resident to make an accurate and early-stage diagnosis of influenza. Furthermore, this makes it possible even for an experienced physician to obtain useful judgment data. Furthermore, improvement of the accuracy diagnosis rate of influenza would enable the patient to finish his/her hospital visit with a single medical examination and receive appropriate medical treatment from an earlier stage.

2-1 Intraoral Imaging Aid

The intraoral imaging aid 3 of the present embodiment will be described in detail with reference to FIGS. 2 to 4.

The intraoral imaging aid 3 is an auxiliary tool used for imaging the inside of the mouth (oral cavity 71 and pharynx 72) of the person 7. More specifically, the intraoral imaging aid 3 is inserted into the oral cavity 71 at the time of intraoral imaging to obtain a good visual field of an imaging region including the oral cavity 71 or the pharynx 72. From the viewpoint of obtaining a better visual field, it is preferable that the intraoral imaging aid 3 has translucency. While the present embodiment assumes a mouthpiece as an example of the intraoral imaging aid 3, the present invention is not limited to this.

Figure 2:
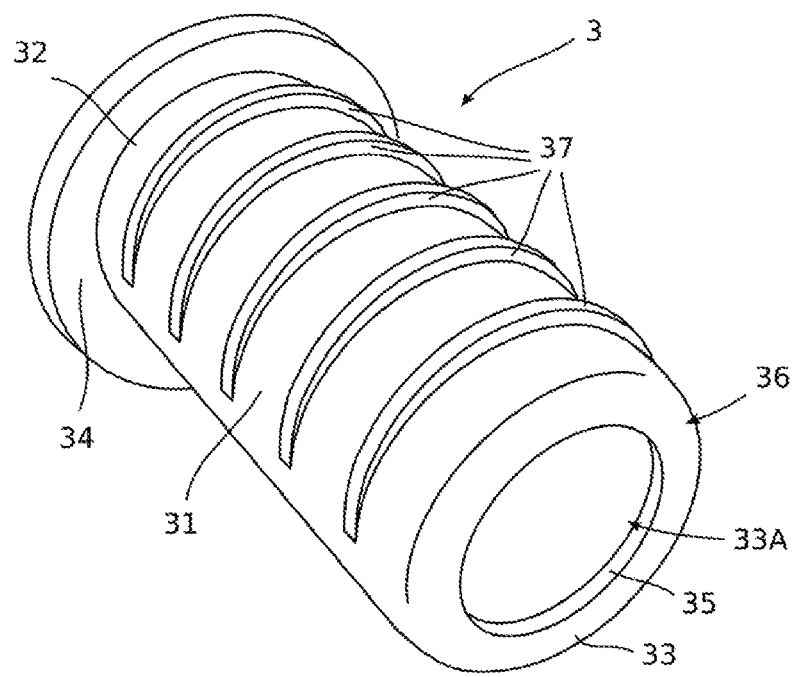
FIG. 2 is a perspective view illustrating the intraoral imaging aid 3 of FIG. 1.

As illustrated in FIG. 2, the intraoral imaging aid 3 includes a main body 31, a flange 34, and a regulator 35. However, the intraoral imaging aid 3 is only required to have the main body 31, and need not necessarily include one or both of the flange 34 and the regulator 35. In the present embodiment, an integrally molded resin product is assumed as the intraoral imaging aid 3. However, the intraoral imaging aid 3 may be formed of other materials such as paper, cloth, or metal or may be formed of a plurality of materials. Furthermore, although the intraoral imaging aid 3 is assumed to be a disposable type, it may be a reusable type.

Figure 21:
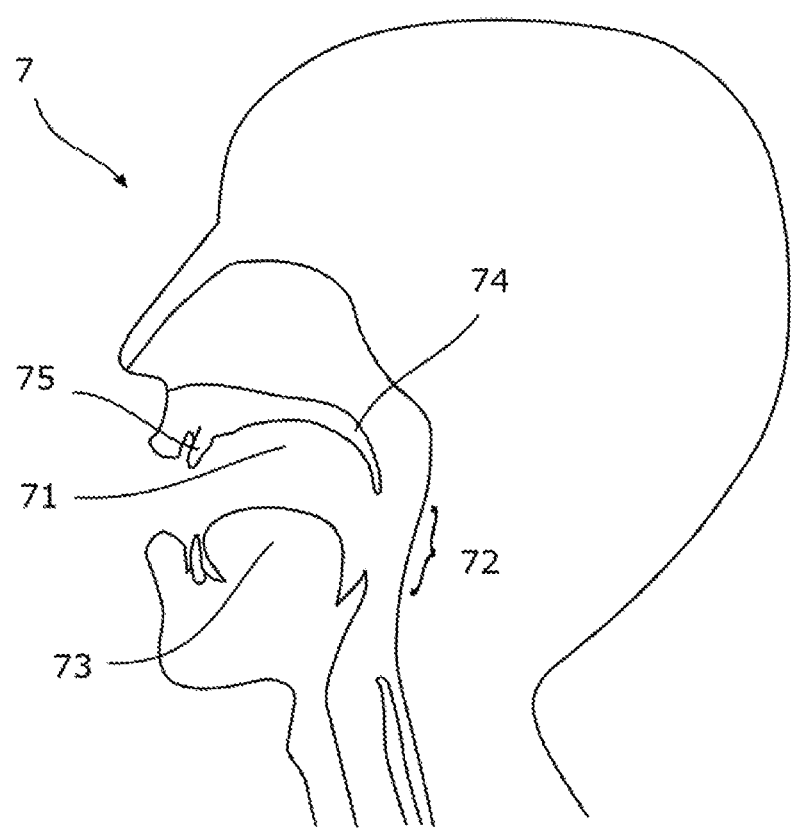
FIG. 21 is a schematic view of a cross-sectional shape of the head of a person 7.
Figure 22:
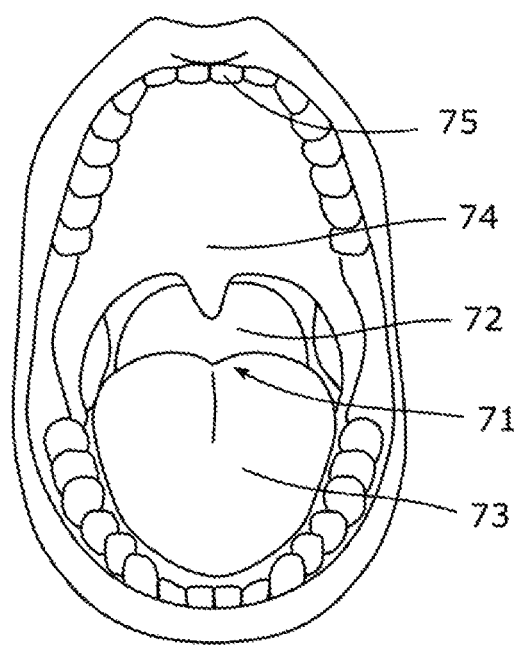
FIG. 22 is a schematic view of the inside of the oral cavity 71.

The main body 31 has a tubular shape as a whole. When the main body 31 is deeply inserted into the oral cavity 71, a tongue 73 is pushed downward and a soft palate 74 is pushed upward, as observed from the comparison of FIGS. 1 and 21, for example. This makes it possible to ensure a good visual field of the pharynx 72 from the inside of the intraoral imaging aid 3 (main body 31) as observed from the comparison between FIG. 4 and FIG. 22, for example.

In the present embodiment, the main body 31 extends substantially linearly. That is, the inner diameter and the outer diameter of the main body 31 are substantially constant in the longitudinal direction. Note that the main body 31 may be partially or entirely curved and the inner diameter or outer diameter of the main body 31 may be changed as long as it would not hinder the sliding of the imaging device 57 on the inner circumferential surface of the main body 31.

The cross-sectional shape of the main body 31 is assumed to be perfectly circular here. However, the cross-sectional shape may be an elliptical shape, a polygonal shape such as a quadrangle, or an asymmetrical shape such as a substantially D shape. When the main body 31 has an elliptical, polygonal, or an asymmetrical cross-sectional shape, the imaging device 57 corresponding to the shape of the main body 31 is regulated or suppressed from a circumferential movement (that is, rotation) centered on an axial direction of the main body 31 when sliding in the main body 31. This makes it possible to obtain equally oriented intraoral images suitable for determination.

As will be described below with reference to FIG. 6, when the main body 31 has a perfectly circular cross-sectional shape, it is allowable to provide rails and protrusions that engage with each other on the outer surface of the imaging device 57 and the inner circumferential surface of the main body 31 so as to regulate rotation of the imaging device 57 within the main body 31.

Figure 3:
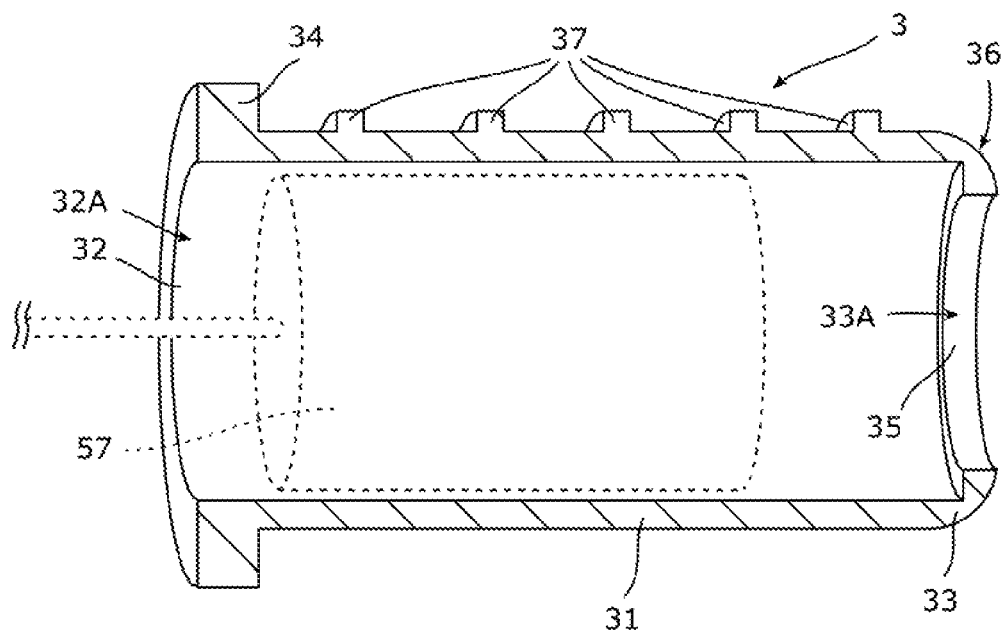
FIG. 3 is a vertical cross-sectional view of the intraoral imaging aid 3 of FIG. 2.
Figure 4:
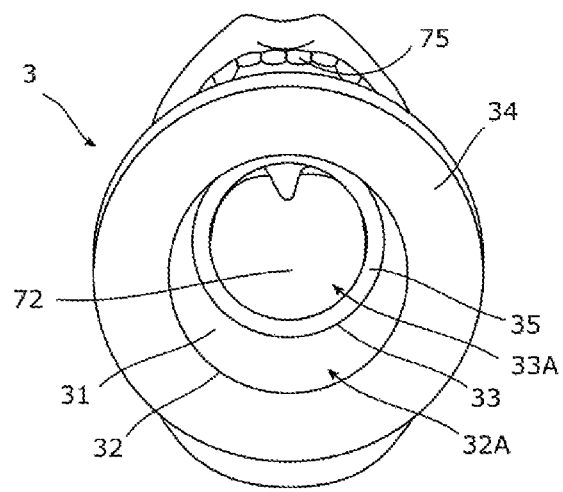
FIG. 4 is a view illustrating an example of a state where the intraoral imaging aid 3 of FIG. 2 is inserted into an oral cavity 71.

As illustrated in FIG. 3, the main body 31 includes ends 32 and 33 located on opposite sides to each other. When the intraoral imaging aid 3 is attached to the oral cavity 71, the end 32 is exposed to the outside while the end 33 is located inside the oral cavity 71. Accordingly, the end 32 corresponds to a first end while the end 33 corresponds to a second end.

The outer circumferential surface of the main body 31 is smooth. The main body 31 and the end 33 are connected to each other via a connecting surface 36 so as to be smoothly and continuously connected to be integrated with each other. That is, the outer surface of the main body 31 is smoothly processed so as not to hurt the oral cavity 71.

The main body 31 has a scale 37. The scale 37 is arranged in the longitudinal direction of the main body 31 and functions as a measure of how deep the main body 31 is inserted into the oral cavity 71. The scale 37 may be provided on either the outer circumferential surface or the inner circumferential surface of the main body 31. When provided on the outer circumferential surface, the scale 37 would be suitably placed on the side coming in contact with the upper lip and upper front teeth 75, that is, on the upper side, as illustrated in FIG. 2. The scales 37 would be suitably arranged at predetermined intervals (in 1 cm intervals, for example). Furthermore, while the scale 37 illustrated in FIG. 2 has a length close to a half circumference in the circumferential direction of the main body 31, it is not limited to this and may be shorter or longer than this.

In the present embodiment, a plurality of raised portions aligned in the longitudinal direction of the main body 31 is assumed as an example of the scale 37. It would be appropriate to previously process the surface of this raised portion to be smooth so as not to hurt the oral cavity of the determination subject 7. Alternatively, the scale 37 may be a substantially linear protrusion extending in the longitudinal direction of the outer circumferential surface of the main body 31 or may be printed or displayed on the outer circumferential surface or the inner circumferential surface of the main body 31, for example.

As illustrated in FIG. 3, the end 32 has an opening 32A, and the imaging device 57 can be inserted into the opening 32A. Accordingly, the imaging device 57 is inserted into the main body 31 through the opening 32A and taken out of the main body 31 through the opening 32A.

The end 32 is provided with the flange 34. The flange 34 extends from the end 32 toward the outside in the radial direction of the main body 31. When the main body 31 enters deep inside the oral cavity 71, the flange 34 comes into contact with the lips or front teeth of the determination subject 7 to prevent the determination subject 7 from swallowing the intraoral imaging aid 3. That is, the flange 34 functions as a stopper. While the flange 34 is provided over the entire circumference of the end 32 in the present embodiment, the flange 34 may be partially formed in the end 32 at positions corresponding to the upper and lower lips, for example. The outer edge of the flange 34 may be perfectly circular as illustrated in FIG. 2, or may be formed in an ellipse, or a polygon such as a quadrangle.

For example, when the determination subject 7 coughs, the droplets from the mouth of the determination subject 7 might be caught by the flange 34. That is, the flange 34 is also useful for the physician to avoid receiving droplets from the determination subject 7. In order to achieve this droplets avoiding function, for example, the shape and size of the flange 34 would be appropriately selected according to the age of use, the physique, or the like.

The end 33 is also open to form a window 33A. The window 33A is provided to give a visual field from the inside of the main body 31 to the outside of the main body 31, and here, the lens of the imaging device 57 in the main body 31 is exposed to the outside. Alternatively, the window 33A may be covered with a transparent member, for example.

The end 33 protrudes toward the inside of the main body 31 and forms the regulator 35. The regulator 35 is provided to come in contact with the imaging device 57 in the main body 31 to regulate the passage of the end 33. Note that the regulator 35 need not be provided on the end 33. For example, a guide 141 (recess or groove), which will be described below in relation to FIG. 6, comes into contact with an engagement protrusion 57A of the imaging device 57 at a terminal end of the guide 141 and regulates the movement of the imaging device 57 to the deeper side, thereby also functioning as the regulator 35.

When imaging the pharynx 72 using the intraoral imaging aid 3 described above, the user inserts the intraoral imaging aid 3 into the oral cavity 71 of the determination subject 7, as illustrated in FIG. 1. At this time, the main body 31 pushes the tongue 73 downward and the soft palate 74 upward. Subsequently or simultaneously, the user inserts the imaging device 57 into the main body 31. At this time, as illustrated in FIG. 4, the tongue 73 and the soft palate 74 do not come into the visual field of the imaging device 57, or even if they do, the range would not be significantly large. Therefore, a good visual field of the pharynx 72 can be obtained.

In addition, the flange 34 can prevent accidental ingestion of the intraoral imaging aid 3 by the determination subject 7. At the same time, the flange 34 can suppress splashing of droplets from the mouth of the determination subject 7 to the user, making it possible to reduce the risk of secondary infection of infectious diseases such as influenza to the user.

Furthermore, the scale 37 enables arrangement of the intraoral imaging aid 3 at an appropriate depth inside the oral cavity according to the physique of the determination subject 7 and the site to be imaged. This contributes to the acquisition of a clear image of the site of interest, as well as achieving suppression of the discomfort and choking of the determination subject 7 caused by inserting the main body 31 more deeply than necessary.

2-2 First Modification of Intraoral Imaging Aid

Figure 5:
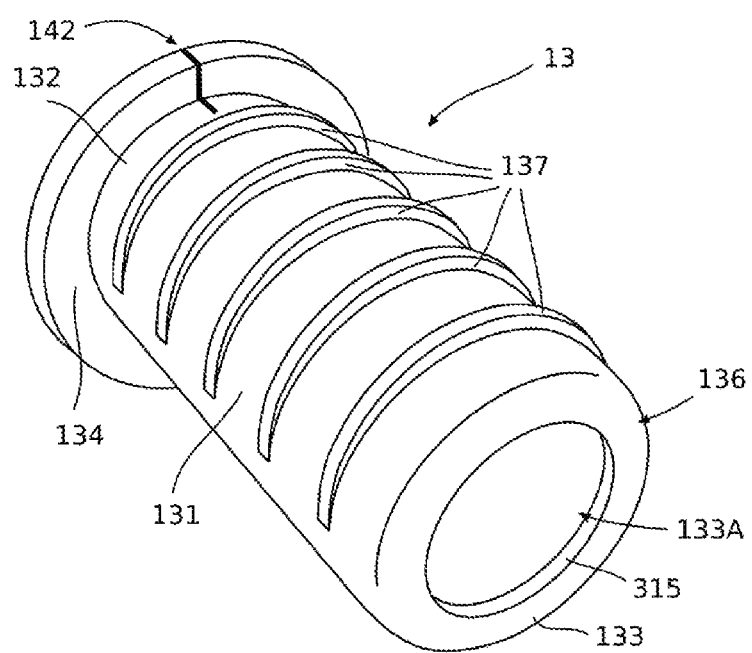
FIG. 5 is a perspective view illustrating an intraoral imaging aid 13 according to a first modification.
Figure 6:
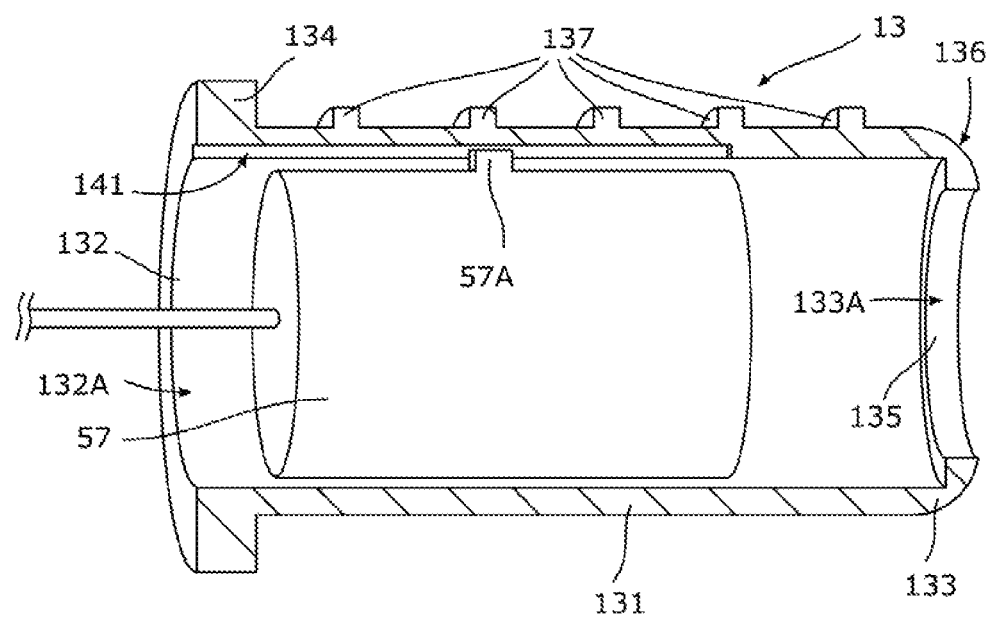
FIG. 6 is a vertical cross-sectional view illustrating the intraoral imaging aid 13 of FIG. 5.
Figure 7:
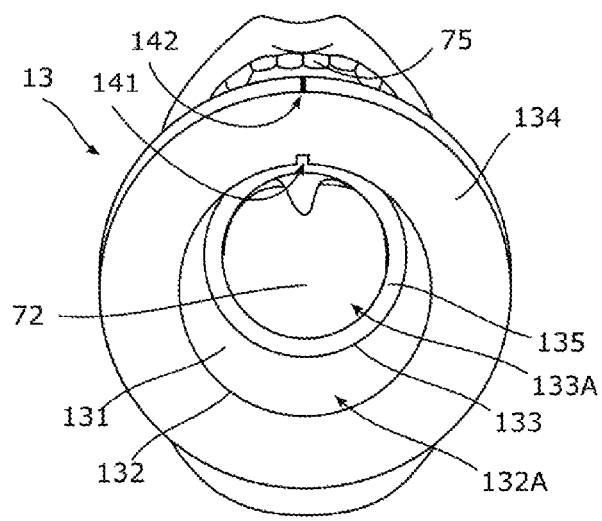
FIG. 7 is a view illustrating an example of a state where the intraoral imaging aid 13 of FIG. 5 is inserted into the oral cavity 71.

With reference to FIGS. 5 to 7, an intraoral imaging aid 13 according to a first modification of the present embodiment will be described.

The intraoral imaging aid 13 has same types of components as the intraoral imaging aid 3 described above and further includes a guide 141 which is substantially linear. In addition, the imaging device 57 includes an engagement protrusion 57A that engages with the guide 141. Accordingly, the guide 141 enables the imaging device 57 to slide inside a main body 131 without rotating with respect to the main body 131.

In the first modification, as illustrated in FIG. 6, one example of the guide 141 is a groove extending substantially linearly from the end 132 to the end 133 so as to correspond to the engagement protrusion 57A on the outer circumferential surface of the imaging device 57. Alternatively, the guide 141 may be a pair of rails protruding from the inner circumferential surface of the main body.

Alternatively, when the cross-sectional shape of the main body 131 is an elliptical shape, a polygonal shape, or an asymmetrical shape such as a substantially D-shape, and the imaging device 57 has an outer shape corresponding to the cross-sectional shape of the main body 131, the imaging device 57 can slide inside the main body 131 without rotating with respect to the main body 131. In this case, the inner circumferential surface of the main body 131 also functions as a guide.

As illustrated in FIG. 5, the outer surfaces of the main body 131 and the flange 134 are provided with an indication display 142 for facilitating the positioning of the main body 131 with respect to the lips of the determination subject 7. As illustrated in FIG. 7, the indication display 142 would be suitably arranged, for example, at a position corresponding to the center of the upper lip or the upper front teeth 75 of the determination subject 7, that is, at the center of the upper portion. For example, when the user attaches the intraoral imaging aid 3 to the oral cavity 71 with the indication display 142 aligned with the center of the upper lip of the determination subject 7, the orientations of the images captured by the imaging device 57 will be substantially the same. This facilitates machine learning using images and the determination process for specific diseases (for example, influenza).

2-3 Second Modification of Intraoral Imaging Aid

Figure 8:
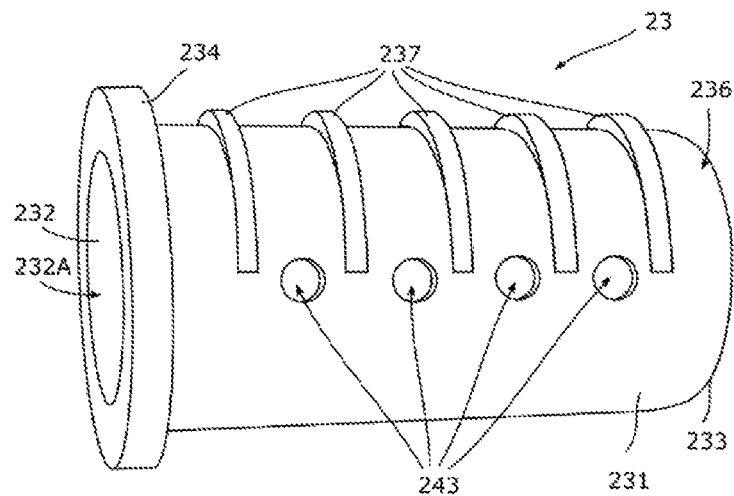
FIG. 8 is a perspective view illustrating an intraoral imaging aid 23 according to a second modification.

With reference to FIG. 8, an intraoral imaging aid 23 according to a second modification of the present embodiment will be described.

The intraoral imaging aid 23 has same types of components as the intraoral imaging aid 3 described above and further includes at least one hole 243 in the main body 231. The hole 243 penetrates between the inside and the outside of the main body 231. The hole 243 makes it easy for the determination subject 7 holding the intraoral imaging aid 23 to breathe, which can bring a sense of security to the determination subject 7. Note that the size, number, and arrangement of the holes 243 may be appropriately set so that the saliva of the determination subject 7 does not easily enter.

The components of the second modification described above, for example, the guide can also be applied to the above-described embodiment and the first modification.

2-4 Third Modification of Intraoral Imaging Aids

Figure 9:
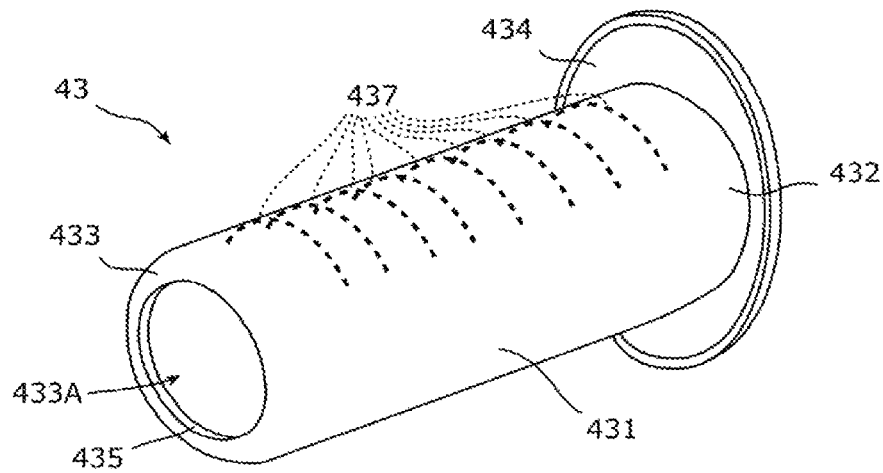
FIG. 9 is a perspective view of an intraoral imaging aid 43 according to a third modification.
Figure 10:
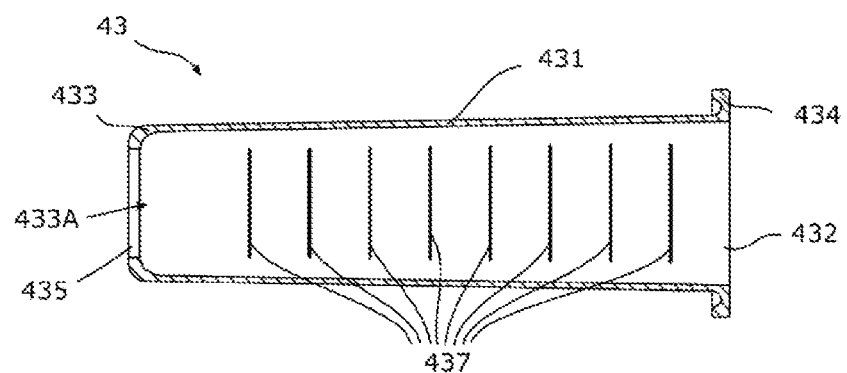
FIG. 10 is a horizontal cross-sectional view of the intraoral imaging aid 43 in FIG. 9.

With reference to FIGS. 9 and 10, an intraoral imaging aid 43 according to a third modification of the present embodiment will be described. The intraoral imaging aid 43 has the same types of components as the intraoral imaging aid 3 described above.

A main body 431 of the intraoral imaging aid 43 is a transparent or translucent resin molded product. Therefore, the imaging region of the intraoral imaging apparatus 5 is wider than the range viewed through a window 433A, making it possible to obtain a wider visual field. Furthermore, the inner diameter of the main body 431 is designed to be slightly smaller from the end 432 toward the end 433, which facilitates resin molding of the intraoral imaging aid 43.

As illustrated in FIG. 10, a scale 437 is formed on the inner circumferential surface of the main body 431, making it possible to form the outer circumferential surface of the main body 431 to be smooth. The scale 437 may be a protrusion protruding from the inner circumferential surface of the main body 431, or a mark displayed or applied on the inner circumferential surface.

As illustrated in FIG. 9, the outer edge of the flange 434 has an elliptical shape that is vertically long, enabling easy positioning of the intraoral imaging aid 43 with respect to the lips of the determination subject 7. Furthermore, the outer edge of the flange 434 is formed so as to protrude toward the end 433 or be thicker than other portions. This ensures the required strength while reducing the amount of material and cost of the flange 434.

2-5 Other Modifications of Intraoral Imaging Aids

The main body 31 need not have substantially the same inner diameter across the portion from the end 32 to the end 33. For example, the main body 31 may be formed to have an inner diameter expanding toward the end 32. The main body 31 having such a trumpet shape will make it possible to stack a plurality of intraoral imaging aids 3 and reduce the space for transportation and storage.

Furthermore, a camera mounted on a smartphone or a tablet terminal may be adopted as the imaging device 57. In order to fix the positional relationship between the camera and the intraoral imaging aid 3 (opening 32A), it is allowable to provide a frame or a clip on the main body 31 or the flange 34. For example, the intraoral imaging aid 3 may include a clip for sandwiching the smartphone from the upper edge or the side edge, or an L-shaped frame for pressing the aid to a corner of the smartphone.

2-6 Example of Packaging of Intraoral Imaging Aids

Figure 11:
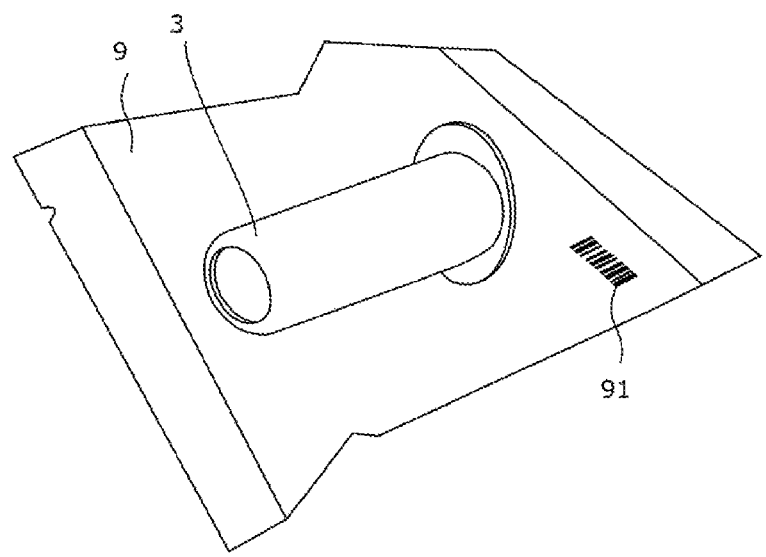
FIG. 11 is a schematic view illustrating the packaged intraoral imaging aid 3.

The intraoral imaging aid 3 may be sterilized and individually packaged in a bag 9 with a display of an identifier 91 as illustrated in FIG. 11, so as to enable hygienic management of the intraoral imaging aid 3. The identifier 91 may be displayed on the intraoral imaging aid 3.

The identifier 91 includes identification information including the product ID of the intraoral imaging aid 3, for example. Examples of the identifier 91 include a bar code and an RF tag, among which a bar code is preferable in consideration of scanning by the intraoral imaging apparatus 5 and use of the medical apparatus 1 in a medical institution. As the barcode, either a one-dimensional barcode or a two-dimensional barcode can be used.

For example, before performing intraoral imaging, the identifier 91 is imaged by the imaging device 57 to read identification information of the intraoral imaging aid 3 in the bag 9 onto the intraoral imaging apparatus 5, enabling confirmation of lot information of the corresponding intraoral imaging aid 3. This makes it possible to ensure traceability even at a time of occurrence of an adverse event to the patient due to the contact with the oral cavity. It is also possible to detect the reuse of the intraoral imaging aid 3, enabling prevention of contamination and secondary infection due to the reuse and ensure safety from a hygienic perspective.

3-1 Intraoral Imaging Apparatus

The intraoral imaging apparatus 5 will be described in detail with reference to FIGS. 12 to 20.

Figure 13:
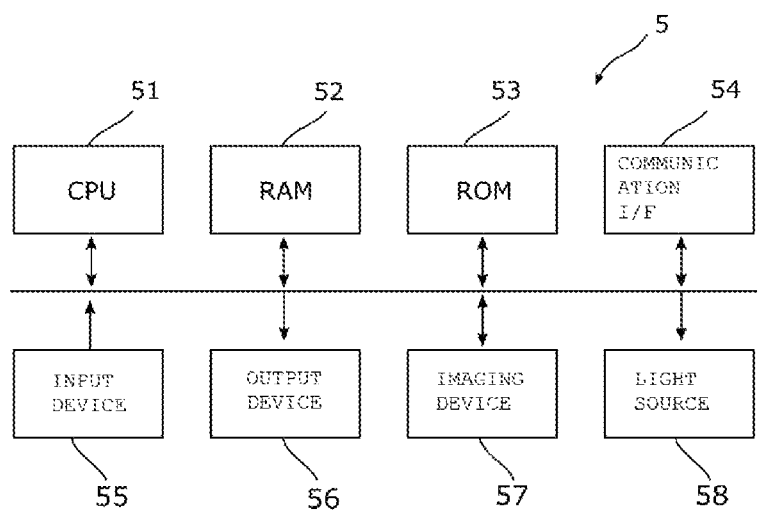
FIG. 13 is a block diagram illustrating an example of a hardware configuration of the intraoral imaging apparatus 5 of FIG. 9.

The intraoral imaging apparatus 5 is a computer including an imaging device, an arithmetic apparatus, and a storage apparatus. Here, it is assumed that the intraoral imaging apparatus 5 includes one computer. However, the apparatus may include a plurality of computers. For example, in remote diagnostic imaging, the imaging function and the determination function may be executed by separate computers. As illustrated in FIG. 13, the intraoral imaging apparatus 5 includes an imaging device 57, a central processing unit (CPU) 51 as an example of an arithmetic apparatus, random access memory (RAM) 52 and read-only memory (ROM) 53 as an example of a storage apparatus, a communication interface 54, an input device 55, an output device 56, and a light source 58.

The communication interface 54 is a wired or wireless communication module so as to be used, for example, for acquiring and updating an application program and a determination algorithm, and collecting (transmitting) captured images. While assumable examples of the wireless communication interface include devices satisfying any of a wireless LAN standard such as Wi-Fi, a short-range wireless communication standard such as BLUETOOTH (trademark), and a third-generation/fourth-generation mobile communication standard, the present invention is not limited to these devices.

Figure 12:
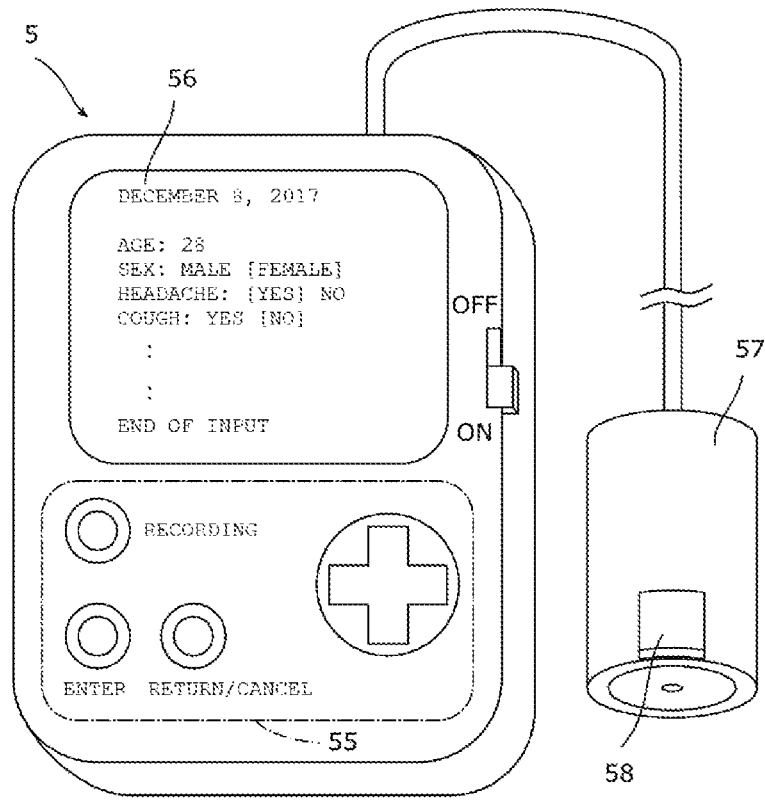
FIG. 12 is a view illustrating an example of an external appearance of the intraoral imaging apparatus 5 of FIG. 1.

The input device 55 is an example of an input apparatus that receives user input, and examples of this include various operation buttons and operation keys as illustrated in FIG. 12. Alternatively, the input device 55 may be another input means such as a touch panel, a microphone, an operation dial, or a stylus. The input device 55 may be arranged in a main body (housing) of the intraoral imaging apparatus 5, or may be arranged in the imaging device 57, for example.

The output device 56 is an example of an output apparatus that outputs a determination result, and examples of this include a display, a speaker, or a printer.

The imaging device 57 acquires an image. In this embodiment, assumable images acquired by the imaging device 57 are moving images. An example of an acquired image size is 640×480 pixels, and an example of a sufficiently usable frame rate is 30 fps. However, the image size and the frame rate are not limited to these.

Alternatively or additionally, the imaging device 57 may be capable of capturing still images. In the case of capturing a still image, the imaging device 57 preferably has a continuous shooting function. However, the present invention is not limited to this.

In the present embodiment, as illustrated in FIG. 12, it is assumed that the imaging device 57 is separated from the main body (housing) of the intraoral imaging apparatus 5 so as to be independently inserted into the intraoral imaging aid 3. The imaging device 57 also preferably has an outer shape (for example, a cylindrical shape) corresponding to the inner circumferential surface of the main body 31 of the intraoral imaging aid 3.

Alternatively, however, the imaging device 57 may be incorporated in the main body of the intraoral imaging apparatus 5, such as a smartphone or a tablet terminal.

The imaging device 57 has an autofocus mechanism (not illustrated), and may have a setting, for example, so that a specific site is in focus in front of the lens. The imaging device 57 may also have a function of automatically recognizing and focusing on a specific site (for example, the posterior pharyngeal wall). The imaging device 57 may further have a zoom function and may be set to capture an image at an appropriate magnification depending on the size of the posterior pharyngeal wall or the follicle, for example.

Light may be emitted from the light source 58 toward the subject during the operation of the imaging device 57, thereby ensuring a high-quality image. Here, the light emitted by the light source 58 may be visible light or invisible light such as near-infrared rays or infrared rays. In addition, for example, it is possible to allow each of a plurality of the light sources 58 to emit a light beam of a specific wavelength range so that one light source emits visible light and the other light sources emit near-infrared rays or infrared rays.

Corresponding to this, it is preferable that the imaging device 57 include light receiving elements of the type and number that can appropriately receive the light emitted from the light source 58. For example, the imaging device 57 would preferably include a light receiving element suitable for receiving visible light in a case where the light source 58 emits visible light; the imaging device 57 would preferably include a light receiving element suitable for receiving invisible light in a case where the light source 58 emits invisible light. Preferable examples of the light source 58 include a light emitting diode (LED) or organic electroluminescence (OEL).

Alternatively, it is allowable to preliminarily program such that an image being captured and a translucent illustration are overlaid on each other on a display as the output device 56 during operation of the imaging device 57. When the user moves the imaging device 57 so that the illustration overlaps the image of the site corresponding to the illustration (for example, palatine uvula or palatine tonsils), it is possible to obtain an appropriate image for determination.

The ROM 53 stores an application program for executing various types of processes in the intraoral imaging apparatus 5 and an algorithm for determining a specific disease. The ROM 53 may also store the image acquired by the imaging device 57, the identification information of the intraoral imaging aid 3, various types of information input from the input device 55 (for example, information of the determination subject 7), and the determination result. The ROM 53 may be a built-in type or a detachable type such as a USB flash drive or a MicroSD card, and may further include a storage region of a storage apparatus of an external computer such as an external server.

The CPU 51 can read the application program stored in the ROM 53 into the RAM 52 and execute various processes including the following processes (a) to (d). Note that the extraction process may be omitted when the image acquired by the imaging device 57 is one still image.

3-2 Main Process Executed by CPU (a) Extraction Process

The CPU 51 extracts at least one still image satisfying a predetermined condition from the image acquired by the imaging device 57. For example, when the imaging device 57 captures a moving image, the CPU 51 extracts at least one still image from a plurality of still images included in the moving image. At the time of capturing a moving image, still images are recorded at a predetermined frame rate. The still images surely include those with good imaging conditions and those with poor imaging conditions. Several images with good imaging conditions are selected as images to be used in the next determination process.

Figure 18:
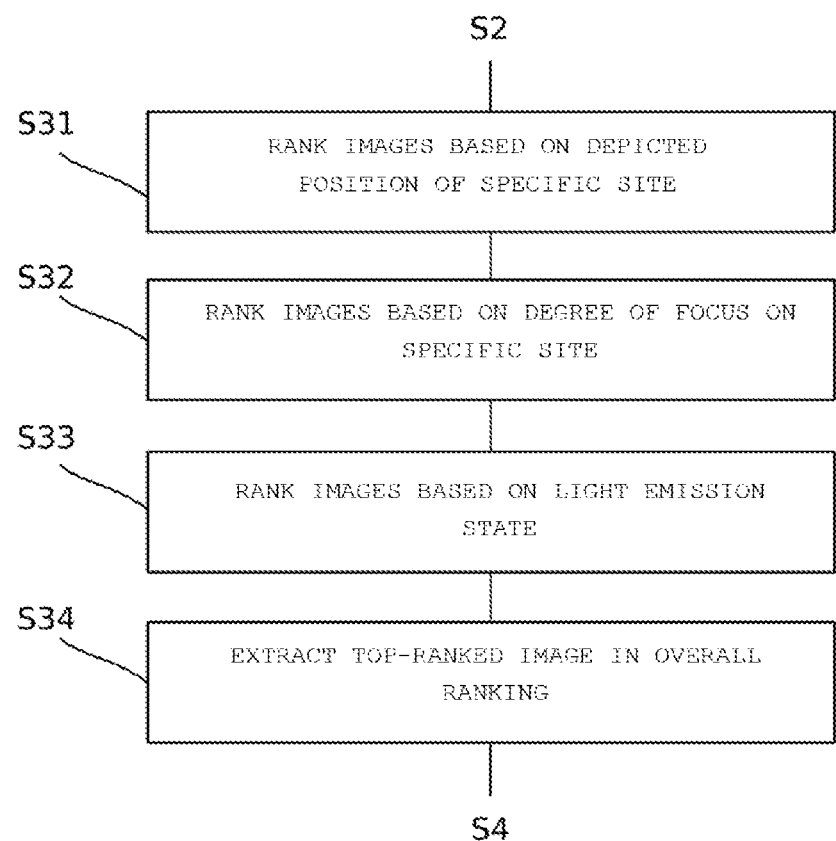
FIG. 18 is a flowchart illustrating an example of an image extraction procedure.

For example, based on a large amount of similar image data, the process would include a work to find conditions that when all or a part of which are satisfied, would make it possible to achieve high diagnostic determination accuracy for a specific disease (for example, influenza), such as a specific imaging angle, a specific light emission state, a specific visual field size, a depicted position of a specific site (for example, pharynx), and the degree of focus on a specific site, and these conditions will be set as a criterion for determining the quality of the imaging conditions. In a case where such a criterion is adopted, the extraction process includes a procedure of ranking the images based on a depicted position of the imaging target (step S31), ranking the images based on the degree of focus on a specific site (step S32), ranking the images based on the light emission state (step S33), and finally selecting a few top-ranked images in the overall ranking (step S34), as illustrated in FIG. 18, for example. Additionally, the images may be ranked according to the criteria of the size of the visual field or the imaging angle before the calculation of the overall ranking. Alternatively, the extraction process may use a deep learning function.

(b) Determination Process

The CPU 51 determines the possibility of a specific disease based on the image acquired from the imaging device (for example, at least one still image obtained by the extraction process) and the determination algorithm stored in the ROM 53. The specific disease is influenza in the present embodiment. For the determination, the information of the determination subject 7 (hereinafter referred to as patient information) input by the user via the input device 55 may be used together. Examples of the patient information include age, sex, elapsed time from onset, presence/absence of various symptoms of influenza (cough, runny nose, chill, or the like), and contact history with other influenza patients. The patient information may include all or part of race and genetic information, date and season, positional information (latitude/longitude of the medical examination location), and meteorological information (for example, weather, temperature).

Figure 17:
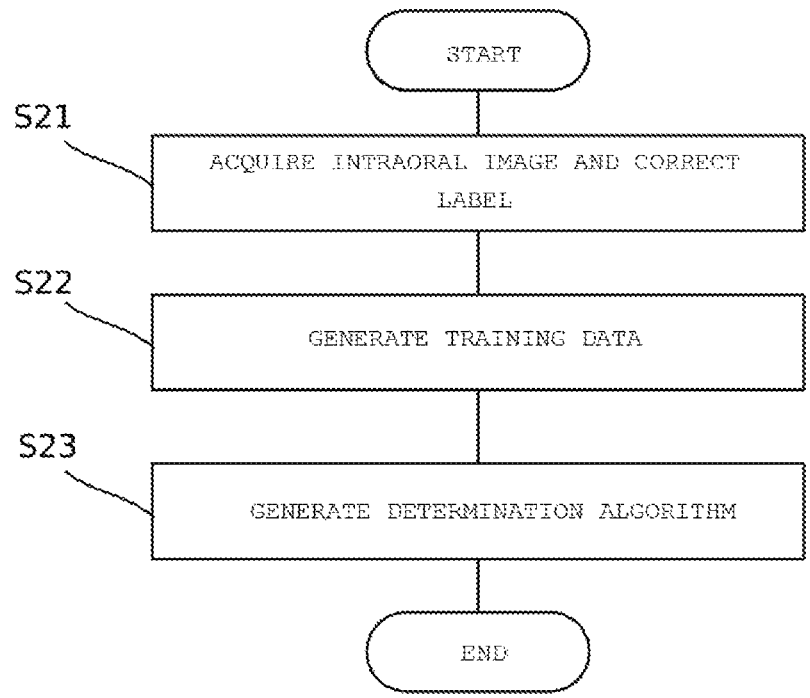
FIG. 17 is a flowchart illustrating a procedure for generating a determination algorithm.

Here, the determination algorithm may be generated using the procedure illustrated in FIG. 17, for example.

For example, in the case of influenza, first, a pharyngeal image of a patient and an accompanying correct label indicating whether the case is influenza are collected in a medical institution (step S21). The correct label is supplied, for example, based on the results of swab influenza rapid test, PCR test, and virus isolation culture test performed on the patient. Even though the PCR test and the virus isolation culture test take several weeks before clarification of the results, these tests can achieve extremely high accuracy and thus their test results are suitable as correct labels. The correct label may include not only the image data but also the above-described patient information.

Next, training data (image data) labeled with the determination result of the PCR test or the virus isolation culture test as the correct data is generated (step S22). Machine learning is performed based on this training data to generate a determination algorithm (step S23). This determination algorithm is an algorithm for determining, after supplied with an image, whether the image indicates high likelihood of influenza. This makes it possible to quantify the probability of influenza, for example, as "98.5%".

Alternatively, the determination may be in the form of positive/negative such as "determination: positive for influenza" and "determination: negative for influenza", for example. In this case, in addition to the positive or negative determination, it is allowable to quantify the reliability or perform indication using a graded evaluation such as high, medium, or low, for the determination. Alternatively, the plausibility of determination of influenza may be indicated by a graded evaluation such as high, medium, or low.

(c) Output Process

The CPU 51 outputs the result of the determination process. Examples of output methods include displaying on a display and transmission to another computer.

(d) Acquisition of Identification Information of Intraoral Imaging Aid

Alternatively, prior to a new determination, the CPU 51 may request the user to input identification information of the intraoral imaging aid 3 to be used for the new determination. For example, when the user images the identifier 91 using the imaging device 57, the CPU 51 acquires identification information of the corresponding intraoral imaging aid 3 from the image of the identifier 91.

Next, the CPU 51 searches records in the ROM 53 to check the presence or absence of a record that matches the corresponding intraoral imaging aid 3. Alternatively, the CPU 51 may control to perform the research of the usage record of the intraoral imaging aid 3 on an external server.

In a case where there is no matching record, the CPU 51 permits new determination. In a case where there is a matching record, the CPU 51 determines that the corresponding intraoral imaging aid 3 has been used before. Accordingly, the CPU 51 may display an alarm on the display or finish the series of processes. That is, the CPU 51 can limit the new determination according to the search result.

3-3 Functional Configuration of Intraoral Imaging Apparatus

Figure 14:
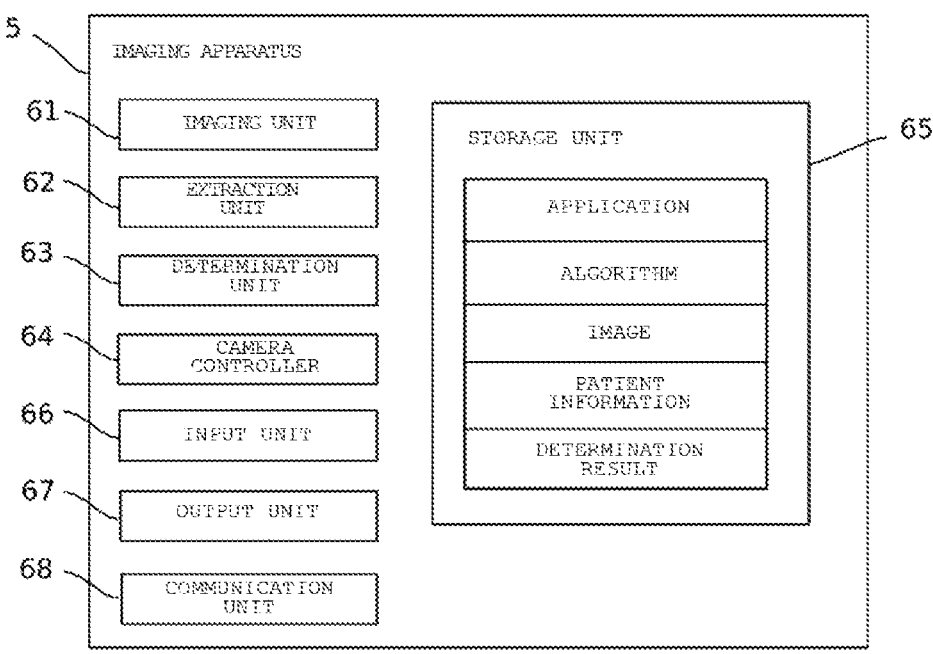
FIG. 14 is a block diagram illustrating an example of a functional configuration of the intraoral imaging apparatus 5 of FIG. 9.

FIG. 14 illustrates a functional configuration of the intraoral imaging apparatus 5. The intraoral imaging apparatus 5 includes an imaging unit 61, an extraction unit 62, a determination unit 63, a camera controller 64, a storage unit 65, an input unit 66, an output unit 67, and a communication unit 68. Regarding the correspondence with the hardware configuration of the intraoral imaging apparatus 5, the imaging unit 61 corresponds to the imaging device 57, the extraction unit 62, the determination unit 63 and the camera controller 64 correspond to the CPU 51, the storage unit 65 to the ROM 53, the input unit 66 to the input device 55, the output unit 67 to the output device 56, and the communication unit 68 to the communication interface 54, individually. Here, the camera controller 64 controls the imaging device 57 to implement various functions such as an auto-focus function and a zoom function.

The intraoral imaging apparatus 5 may include other functions such as a clocking function for acquiring the time at which imaging was performed, a positional information acquisition function for acquiring the positional information at which the imaging was performed, and a meteorological information acquisition function for acquiring the meteorological information at the position. The clocking function may be implemented as a built-in clock or may be one of functions of a communication interface that makes access to an external time server. The positional information acquisition function may be implemented as a global positioning system (GPS), for example. The meteorological information acquisition function may be one of functions of a communication interface that makes access to an external meteorological server.

3-4 Operation Example 1 of Intraoral Imaging Apparatus

Figure 15:
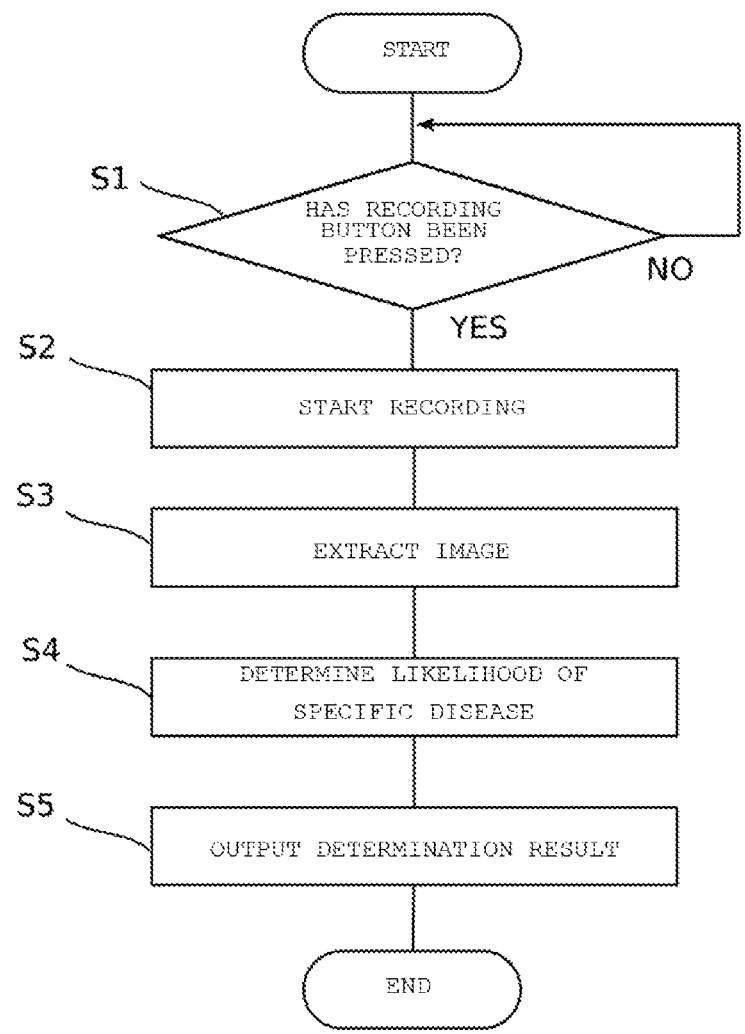
FIG. 15 is a flowchart illustrating operation example 1 of the intraoral imaging apparatus 5 in FIG. 9.

Operation example 1 of the intraoral imaging apparatus 5 will be described with reference to FIG. 15. Here is an example of an operation when the intraoral imaging apparatus 5 captures a moving image. Note that the intraoral imaging apparatus 5 may capture a still image, and in this case, the intraoral imaging apparatus 5 operates similarly.

When the power is turned on, the intraoral imaging apparatus 5 starts imaging using the imaging device 57 and displays an image on the display, and determines in step S1 whether the recording button (one of the input devices 55) has been pressed. When the pressing of the recording button has not been confirmed, the intraoral imaging apparatus 5 repeats step S1.

When the pressing of the recording button has been confirmed, the intraoral imaging apparatus 5 starts recording in step S2. Together with this, the intraoral imaging apparatus 5 turns on the light source 58. The user attaches the intraoral imaging aid 3 to the oral cavity 71 of the determination subject 7 and then inserts the imaging device 57 into the intraoral imaging aid 3 (refer to FIG. 1). The imaging device 57 images the intraoral portions (oral cavity 71 or pharynx 72) of the determination subject 7 while the intraoral imaging aid 3 is sliding.

In step S3, the intraoral imaging apparatus 5 extracts a still image appropriate for determination from the plurality of still images included in the acquired moving image. At this time, the extracted still image may be displayed on the display as the extraction result.

In step S4, the intraoral imaging apparatus 5 determines the likelihood of a specific disease based on the extracted still image and the determination algorithm and then outputs in step S5 the determination result to the display, for example. This completes a series of operations.

In this manner, the possibility of a specific disease is evaluated using the determination algorithm generated by machine learning, and thus, a highly accurate determination result can be expected.

The image captured with good imaging conditions is selected for the determination, leading to improvement of the determination accuracy.

The use of the intraoral imaging apparatus 5 in combination with the intraoral imaging aid 3 enables acquisition of an image with a wide visual field and high clarity. This contributes to the improvement of determination accuracy.

3-5 Operation Example 2 of Intraoral Imaging Apparatus

Figure 16:
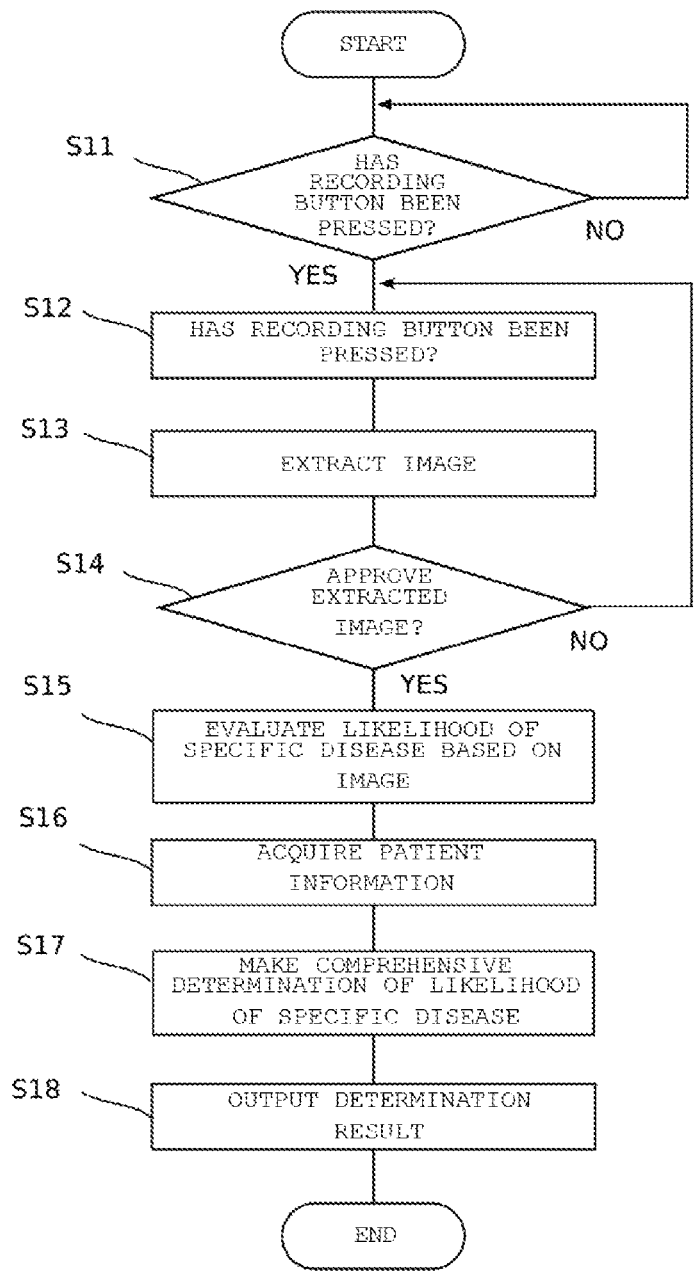
FIG. 16 is a flowchart illustrating operation example 2 of the intraoral imaging apparatus 5 in FIG. 9.

Operation example 2 of the intraoral imaging apparatus 5 will be described with reference to FIG. 16. Operation example 2 includes the same steps as operation example 1 described above, and further includes a step of confirming the extracted image by the user (S14), a step of inputting patient information (S16), and a comprehensive determination (S17).

Specifically, when the power is turned on, the intraoral imaging apparatus 5 confirms the pressing of the recording button (step S11), starts recording (step S12), and extracts an image for determination (step S13). Subsequently, the intraoral imaging apparatus 5 displays the extracted image on a display, for example, and asks the user to confirm whether to use the image for determination (step S14). When the user selects "NO", steps S12 and S13 are executed again, and a new image for determination is presented to the user.

When the user selects "YES" in step S14, the intraoral imaging apparatus 5 determines the likelihood of a specific disease based on the extracted image (step S15).

Next, the intraoral imaging apparatus 5 requests the user to input patient information (step S16). Here, the patient information is stylized and simple information such as the body temperature at the time of examination and the presence or absence of vaccination. Such patient information is input in a form that can be uniformly processed by software, as illustrated in FIG. 9. For example, it is allowable to use a pull-down menu or an input form setting that rejects inputs other than single-byte numerals. Alternatively, the intraoral imaging apparatus 5 may acquire the patient information from an external computer (for example, an electronic medical chart system) via a wired or wireless channel. Note that step S16 may be executed prior to step S11.

Subsequently, both the patient information and the evaluation of the likelihood of a specific disease based on the image are integrated to calculate the overall likelihood of the disease (step S17). The calculation result is displayed on the display, for example (step S18) to complete the series of procedures.

In this manner, the intraoral imaging apparatus 5 evaluates the possibility of a specific disease based on the image confirmed by the user, thereby improving the accuracy and reliability of the determination.

Furthermore, by performing the determination based on the patient information, further enhancement in the accuracy and reliability of the determination will be expected.

3-6 Operation Example 3 of the Intraoral Imaging Apparatus

Figure 19:
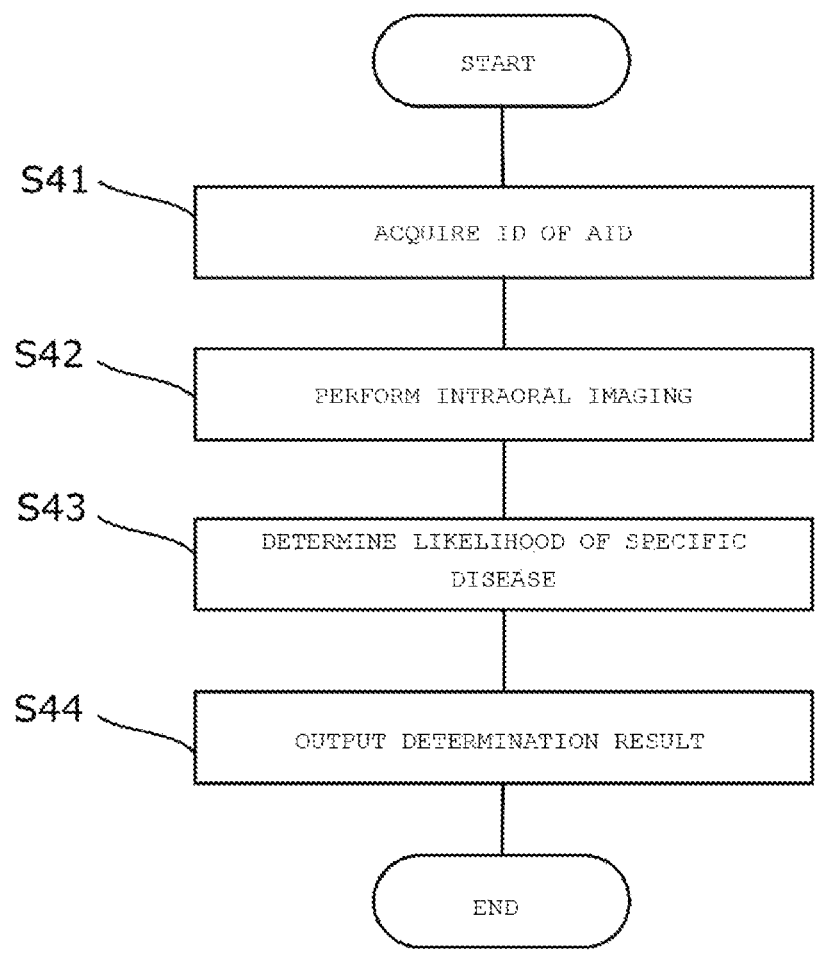
FIG. 19 is a flowchart illustrating operation example 3 of the intraoral imaging apparatus 5 in FIG. 9.

Operation example 3 of the intraoral imaging apparatus 5 will be described with reference to FIG. 19. Operation example 3 includes a procedure (step S41) of acquiring identification information of the intraoral imaging aid 3.

Specifically, after the power is turned on, the intraoral imaging apparatus 5 requests the user to input identification information of the intraoral imaging aid 3 in step S41, for example, via displaying onto the display. For example, after the user images the identifier 91 on the bag 9 using the imaging device 57 or inputs identification information via the input device 55, the intraoral imaging apparatus 5 acquires identification information of the intraoral imaging aid 3.

The intraoral imaging apparatus 5 may check the lot information of the intraoral imaging aid 3 by using the identification information. For example, the intraoral imaging apparatus 5 may search whether the record in the ROM 53 includes the product ID of the intraoral imaging aid 3, or may cause an external computer to check the presence or absence of the product ID.

In a case where the corresponding product ID exists in the internal or external record, the intraoral imaging apparatus 5 may output an alarm or terminate the series of processes. Examples of the alarm include displaying on the display indicating that the intraoral imaging aid 3 has been used. This would restrict the reuse of the intraoral imaging aid 3, leading to enhancement of the safety of the intraoral imaging aid 3 including prevention of secondary infection. In addition, this makes it possible to form one-to-one correspondence between the intraoral imaging aid 3 and the determination subject 7 who uses the aid, facilitating a follow-up survey in the future.

Thereafter, the intraoral imaging apparatus 5 performs intraoral imaging in step S42. Here, the intraoral imaging process may be the same as in the above-described operation examples 1 and 2, or may be performed in the procedure described below. The intraoral imaging apparatus 5 next determines the likelihood of a specific disease in step S43 and outputs the determination result in step S44 to end the series of processes.

3-7 Another Example of Intraoral Imaging

Figure 20:
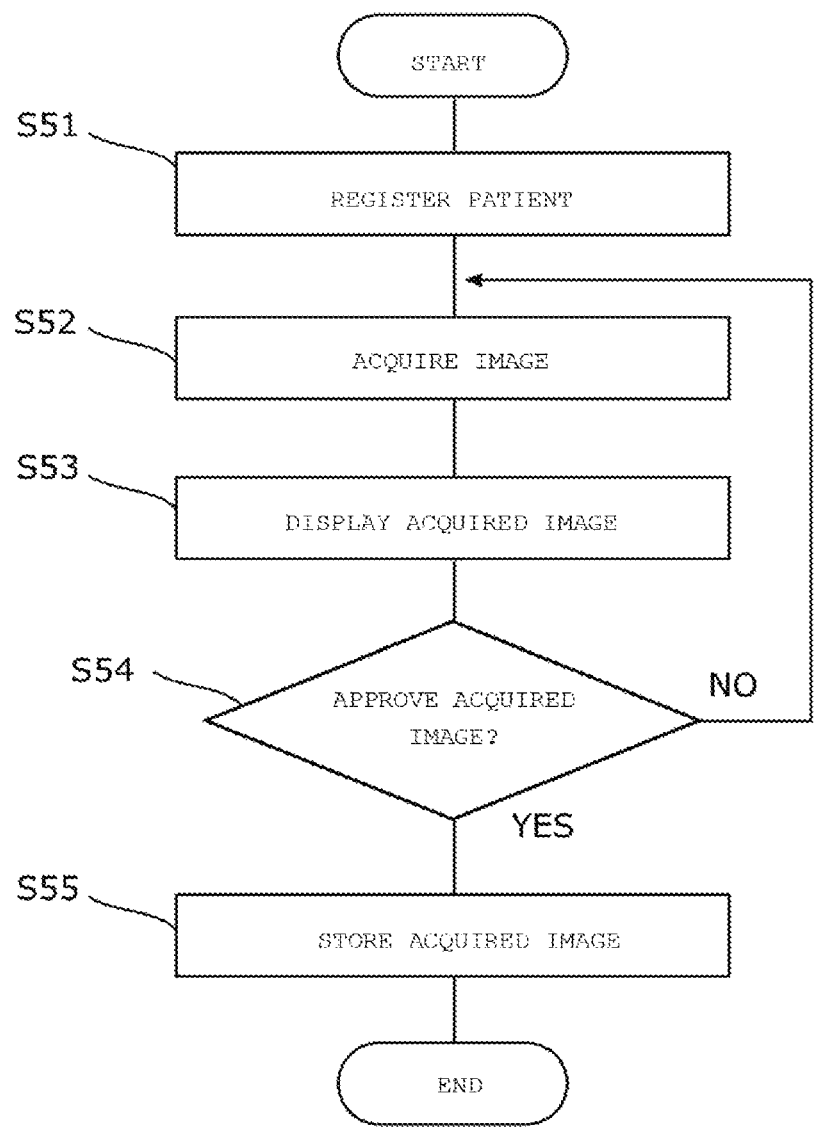
FIG. 20 is a flowchart illustrating an example of an imaging operation of the intraoral imaging apparatus 5.

Another procedure of intraoral imaging will be described with reference to FIG. 20. The procedure described here can be replaced with the image acquisition procedure in the above-described operation examples 1 to 3. This procedure can also be used to collect training data for machine learning.

First, in step S51, the intraoral imaging apparatus 5 performs patient registration. The patient registration is performed by recording the patient ID input or imaged by the user in the intraoral imaging apparatus 5.

Next, in step S52, the intraoral imaging apparatus 5 acquires an image. The image here is a still image and may be formed with a set of still images extracted at predetermined time intervals (for example, every one second) from the images captured by the imaging device 57.

Subsequently in step S53, the intraoral imaging apparatus 5 displays the acquired image on a display, for example, and asks the user for confirmation. When approval is obtained from the user in step S54, the intraoral imaging apparatus 5 saves the approved image in step S55 to complete the series of imaging processes. In a case where the user's approval is not obtained, the process returns to step S52 to acquire the image again.

While the representative embodiments of the present invention have been described above, the present invention is not limited to these, and various design changes are possible, which are also included in the present invention. As described above, the present invention can also be applied to the determination of diseases such as streptococcal infections, adenovirus infections, EB virus infections, *mycoplasma* infections, or the like, having differences in the pharyngeal or oral cavity findings.

The invention claimed is:

1. An intraoral imaging apparatus comprising:
   an imaging device configured to acquire an intraoral image;
   a light source configured to emit light to a subject of the imaging device;
   a memory configured to store a program and an algorithm for performing determination of an infection disease; and
   a processor configured to execute the program so as to:
      determine a possibility of the infection disease based on the intraoral image and the algorithm; and
      output a result of the determination of the possibility of the infection disease.

2. The intraoral imaging apparatus according to claim 1, wherein the imaging device is configured to acquire a moving image as the intraoral image, and the moving image includes a plurality of still images, and
   the processor is configured to:
      extract at least one still image from the plurality of still images, and the at least one still image satisfies a predetermined condition, and
      determine the possibility of the infection disease based on a result of the extraction of the at least one still image.

3. The intraoral imaging apparatus according to claim 1, further comprising:
   an input interface configured to receive an input of patient information,
   wherein the processor is configured to determine the possibility of the infection disease based on the patient information.

4. The intraoral imaging apparatus according to claim 2, further comprising:
   a display configured to display at least one of the intraoral image or the result of the extraction.

5. The intraoral imaging apparatus according to claim 1,
   wherein the imaging device acquires the intraoral image at a position inside an intraoral imaging aid having a tubular shape, and the intraoral imaging aid is attached to an inside of a mouth of a patient,
   the memory is configured to store identification information of the intraoral imaging aid that has already been used, and
   the processor is further configured to:
      acquire the identification information of a new intraoral imaging aid to be used for new determination of the possibility of the infection disease;

search presence or absence of a record in the memory that matches the identification information of the new intraoral imaging aid; and restrict the new determination depending on a result of the search.

6. A medical apparatus comprising:

the intraoral imaging apparatus according to claim 1; and an intraoral imaging aid having a tubular shape and configured to be detachably attached to an inside of a mouth of a patient, wherein the intraoral imaging aid includes:

a first end having an opening; and a second end located on an opposite side of the first end and having a window that provides a visual field from an inside to an outside of the intraoral imaging aid.

7. A computer program product embodying computer readable instructions stored on a non-transitory computer-readable storage medium for causing a computer including a memory storing an algorithm for performing determination of an infection disease and a processor to execute a process by the processor so as to perform the steps of:

determining a possibility of the infection disease based on an intraoral image acquired by an imaging device and based on the algorithm; and outputting a result of the determination of the possibility of the infectoin disease.

8. The intraoral imaging apparatus according to claim 2, further comprising:

an input interface configured to receive an input of patient information, wherein the processor is configured to determine the possibility of the infection disease based on the patient information.

9. The computer program product according to claim 7, further comprising:

acquiring a moving image as the intraoral image, the moving image including a plurality of still images;

extracting at least one still image from the plurality of still images, the at least one still image satisfying a predetermined condition; and determining the possibility of the infection disease based on a result of the extraction of the at least one still image.

10. The computer program product according to claim 7, further comprising:

receiving an input of patient information, wherein the processor is configured to determine the possibility of the infection disease based on the patient information.

11. The computer program product according to claim 8, further comprising:

displaying at least one of the intraoral image or the result of the extraction on a display.

12. The computer program product according to claim 7, wherein the processor is configured to acquire the intraoral image at a position inside an intraoral imaging aid having a tubular shape, and the intraoral imaging aid is attached to an inside of a mouth of a patient, the memory is configured to store identification information of the intraoral imaging aid that has already been used, and the processor is further configured to:

acquire the identification information of a new intraoral imaging aid to be used for new determination of the possibility of the infection disease;

search presence or absence of a record in the memory that matches the identification information of the new intraoral imaging aid; and restrict the new determination depending on a result of the search.

* * * * *